(12) United States Patent
Kim

(10) Patent No.: US 11,938,162 B2
(45) Date of Patent: Mar. 26, 2024

(54) **COMPOSITION FOR PREVENTING OR TREATING DRY EYE SYNDROME, CONTAINING *AUCUBA JAPONICA* EXTRACT**

(71) Applicant: INDUSTRIAL COOPERATION FOUNDATION CHONBUK NATIONAL UNIVERSITY, Jeonju-si (KR)

(72) Inventor: Jung Hyun Kim, Jeonju-si (KR)

(73) Assignee: INDUSTRIAL COOPERATION FOUNDATION CHONBUK NATIONAL UNIVERSITY, Jeonju-si (KR)

( * ) Notice: Subject to any disclaimer, the term of this patent is extended or adjusted under 35 U.S.C. 154(b) by 445 days.

(21) Appl. No.: 16/965,754

(22) PCT Filed: Oct. 30, 2018

(86) PCT No.: PCT/KR2018/012976
§ 371 (c)(1),
(2) Date: Jul. 29, 2020

(87) PCT Pub. No.: WO2019/146881
PCT Pub. Date: Aug. 1, 2019

(65) Prior Publication Data
US 2021/0030828 A1 Feb. 4, 2021

(30) Foreign Application Priority Data
Jan. 29, 2018 (KR) .................. 10-2018-0010843

(51) Int. Cl.
*A61P 27/04* (2006.01)
*A61K 36/00* (2006.01)
*A61K 36/54* (2006.01)

(52) U.S. Cl.
CPC .............. *A61K 36/54* (2013.01); *A61P 27/04* (2018.01); *A61K 2236/331* (2013.01)

(58) Field of Classification Search
None
See application file for complete search history.

(56) References Cited

U.S. PATENT DOCUMENTS

PP14,744 P3 * 5/2004 Yamaguchi .............. A01H 6/00
Plt./226
2004/0197272 A1 * 10/2004 Fischer .............. A61K 31/7048
514/474

FOREIGN PATENT DOCUMENTS

| CN | 101974049 A | * | 2/2011 |
| KR | 10-2015-0050778 A | | 5/2015 |
| KR | 2015050778 A | * | 5/2015 |
| KR | 10-2015-0135528 A | | 12/2015 |
| KR | 10-2016-0111646 A | | 9/2016 |
| KR | 10-1762797 B1 | | 7/2017 |
| KR | 10-1764377 B1 | | 8/2017 |
| KR | 10-1849301 B1 | | 4/2018 |

OTHER PUBLICATIONS

Eunsoo Jung et al. ("*Aucuba japonica* extract inhibits retinal neovascularization in a mouse model of oxygen-induced retinopathy, with its bioactive components preventing VEGF-induced retinal vascular hyperpermeability" Food Sci Nutr. 2020:8:2895-2903, Accepted Mar. 30, 2020) (Year: 2020).*
Kang WS, et al. "*Aucuba japonica* Extract and Aucubin Prevent Desiccating Stress-Induced Corneal Epithelial Cell Injury and Improve Tear Secretion in a Mouse Model of Dry Eye Disease", Molecules, Oct. 11, 2018,23,2599,pp. 1-10; doi:10.3390/molecules23102599 (Year: 2018).*
International Search Report dated May 8, 2019 in corresponding International Patent Application No. PCT/KR2018/012976 (2 pages in English, 2 pages in Korean).

* cited by examiner

*Primary Examiner* — Aaron J Kosar
*Assistant Examiner* — Randall O Winston
(74) *Attorney, Agent, or Firm* — NSIP Law

(57) ABSTRACT

Provided is a composition for preventing, alleviating or treating dry eye syndrome, containing an *Aucuba japonica* extract as an active ingredient. The composition containing an *Aucuba japonica* extract can be effectively used in the prevention, alleviation or treatment of dry eye syndrome.

18 Claims, 3 Drawing Sheets

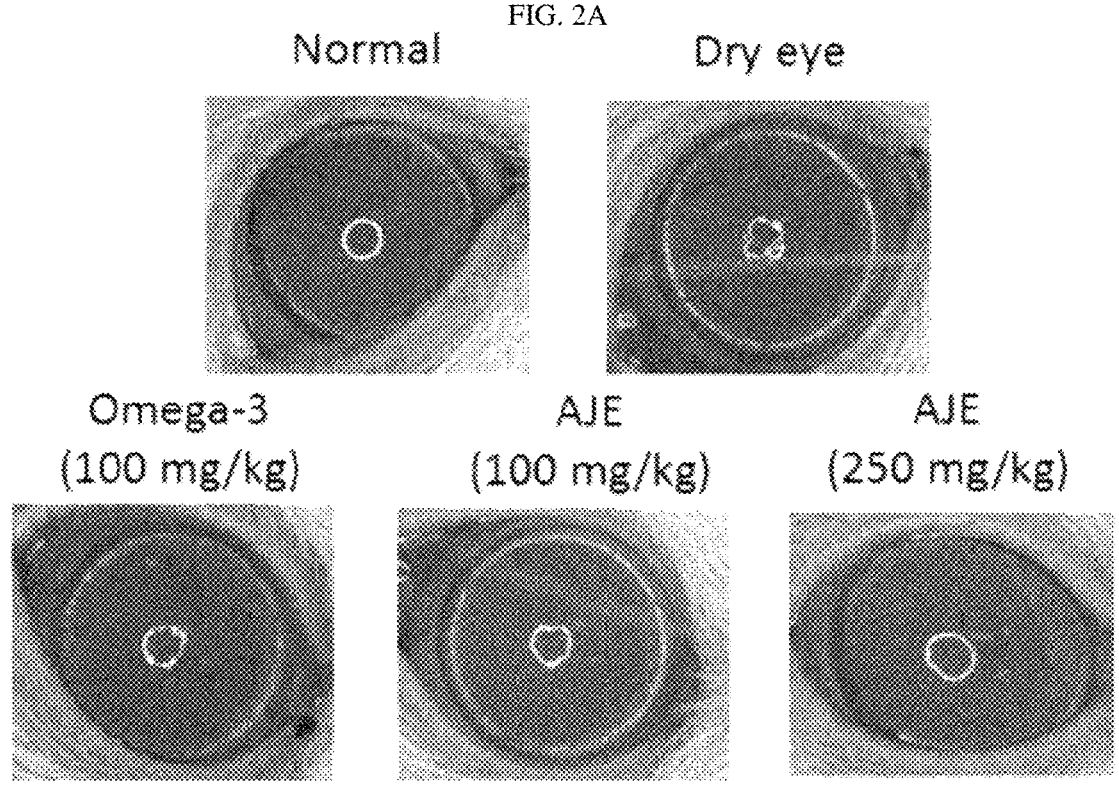

COMPOSITION FOR PREVENTING OR TREATING DRY EYE SYNDROME, CONTAINING *AUCUBA JAPONICA* EXTRACT

CROSS REFERENCE TO RELATED APPLICATIONS

This application is a U.S. National Stage Application of International Application No. PCT/KR2018/012976, filed on Oct. 30, 2018, which claims the benefit under 35 USC 119(a) and 365 (b) of Korean Patent Application No. 10-2018-0010843, filed on Jan. 29, 2018, in the Korean Intellectual Property Office, the entire disclosure of which is incorporated herein by reference for all purposes.

TECHNICAL FIELD

The present disclosure relates to a composition for preventing, alleviating or treating dry eye syndrome.

BACKGROUND ART

Dry eye syndrome (dry eye) is a common disease occurring in around 20% of Korean adults. Its incidence is increasing consistently due to global climate change and environmental pollution. Dry eye syndrome causes not only simple tear deficiency but also eye discomfort caused by inflammation of the ocular surface (the cornea and the conjunctiva), impaired vision, and damage to the ocular surface due to induced instability of the tear film. In addition, dry eye syndrome is highly likely to induce pain, irregular corneal surface, blurred and fluctuating vision, and many ocular diseases such as corneal ulcer, etc. Although the mechanism of the onset of dry eye syndrome has not been fully elucidated, it is reported that infiltration of inflammatory cells, increased expression of immune-activating molecules and adhesion molecules, Th1 and Th17 responses, abnormal change in apoptotic markers and chemokines, etc. play an important role in inflammation. In general, consumption of foods rich in potassium and anthocyanins is recommended for the treatment of dry eye syndrome. In addition, the intake of fruits such as kale, kiwi, apple, etc. is highly recommended. Furthermore, artificial tears or medications that regulate the secretion amount of tears by blocking lacrimal points are often used. However, these prescriptions are temporary and no special therapeutic agent or functional food is available yet.

*Aucuba japonica* is a broadleaf shrub in the family Garryaceae, growing in the southern coast and Jeju Island of Korea. It grows mainly in warm mountain areas, and is a representative type of temperate forests in the southern part of Korea, especially in Ulleungdo area. The fruit of *Aucuba japonica* is beautiful and popular for ornamental use. Its leaf and bark are used for medicinal purposes. It is called peach leaf coral, acuba leaf or blue tree. Traditionally, *Aucuba japonica* has been used to treat neuralgia or inflammations such as arthritic gout.

The inventors of the present disclosure have searched for a composition for preventing and treating dry eye syndrome from natural products. In doing so, they have completed the present disclosure by identifying that an *Aucuba japonica* extract or a fraction thereof can treat dry eye syndrome by increasing the amount of tear secretion and inhibiting the change of corneal morphology.

DISCLOSURE

Technical Problem

The present disclosure provides a pharmaceutical composition for preventing or treating dry eye syndrome, which contains an *Aucuba japonica* extract as an active ingredient.

The present disclosure also provides a functional health food composition for preventing or alleviating dry eye syndrome, which contains an *Aucuba japonica* extract as an active ingredient.

Technical Solution

In an aspect, the present disclosure provides a pharmaceutical composition for preventing or treating dry eye syndrome, which contains an *Aucuba japonica* extract as an active ingredient. In another aspect, the present disclosure provides a functional health food composition for preventing or alleviating dry eye syndrome, which contains an *Aucuba japonica* extract as an active ingredient.

"*Aucuba japonica*" refers to a species of dicotyledonous evergreen tree of the genus *Aucuba*, the family Garryaceae, the order Garryales. It is distributed mainly in the southern part of Korea, especially in Ulleungdo area. It is called peach leaf coral, acuba leaf or blue tree.

"Dry eye syndrome" refers to an ocular disease in which the ocular surface is damaged due to lack of tears, excessive evaporation of tears, or imbalance in tear composition. Generally, it causes irritation symptoms such as eye irritation soreness, irritation, foreign body sensation, dryness, etc.

The extract may be an extract extracted with a solvent from the whole aerial part of the *Aucuba japonica*, a part thereof, or a material derived therefrom. The part may be a stem, leaf, flower, petal or seedling of *Aucuba japonica*. The whole plant of *Aucuba japonica*, a part thereof, or a material derived therefrom used for the extraction may be ground, chopped or dried suitably.

The extract may be extracted using water, acetone, an alcohol, for example, a $C_1$-$C_6$ alcohol, or a mixture thereof as a solvent. The $C_1$-$C_6$ alcohol may be methanol, ethanol, propanol, isopropanol, 1,3-propanediol, butanol, pentanol, hexanol, etc. The solvent may be, for example, a mixture of water and an alcohol, i.e., an aqueous alcohol solution. The alcohol concentration of the aqueous alcohol solution may be 1-100 (w/w) %, e.g., 1-99.5 (w/w) %, 10-100 (w/w) %, 20-100 (w/w) %, 20-80 (w/w) %, 20-60 (w/w) %, 20-40 (w/w) % or 30 (w/w) %. The aqueous alcohol solution may be an aqueous solution of methanol, ethanol or butanol.

The extraction may be performed by warmed liquid extraction, pressurized liquid extraction (PLE), microwave-assisted extraction (MAE), subcritical extraction (SE) or a combination thereof. The subcritical extraction may be subcritical water extraction (SWE). The superheated water extraction is also referred to as superheated water extraction or pressurized hot water extraction (PHWE). The warmed liquid extraction may be reflux extraction.

The extraction may be carried out at 4-70° C., e.g., at 4-50° C., 4-40° C., 4-30° C., 10-70° C., 15-70° C., 20-70° C., 4-50° C., 10-50° C., 4-40° C., 4-30° C., 10-40° C., 10-35° C. or 10-30° C. If the extraction is warmed extraction, it may be carried out at a temperature at which the solvent used for the extraction boils, or at a temperature at which the desired components are extracted from the plant. For example, it may be carried out at 40° C. or higher, 50° C. or higher, 60° C. or higher, 70° C. or higher, 80° C. or higher, 90° C. or higher, 100° C. or higher, 120° C. or higher, 140° C. or higher, 160° C. or higher, or 200° C. or higher. As a specific example, water may be used as a solvent and the extraction may be carried out at a temperature of 90-120° C. The time required for the extraction may vary depending on the selected temperature, and may range from 1 hour to 2 months, e.g., from 1 hour to 1 month, from 1 hour to 15 days, from 1 hour to 10 days, from 1 hour to 5 days, from 1 hour to 3 days, from 1 hour to 2 days, from 1 hour to 1 day, from 5 hours to 1 month, from 5 hours to 15 days, from 5 hours to 10 days, from 5 hours to 5 days, from 5 hours to 3 days, from 5 hours to 2 days, from 5 hours to 1 day, from 10 hours to 1 month, from 10 hours to 15 days, from 10 hours to 10 days, from 10 hours to 5 days, from 10 hours to 3 days, or from 10 hours to 2 days. The extraction may include mixing the whole aerial part of *Aucuba japonica*, a part thereof, a seedling thereof, or a material derived therefrom into the solvent and leaving the mixture alone for a predetermined time. The mixture may be stirred adequately during the period. The extraction may be repeated one or more times, for example, 1 to 5 times.

The extraction may further include a process of separating the plant residue and the extract by a known method such as filtration, etc. The extraction can also include removing the solvent from the obtained extract by a known method such as concentration under reduced pressure. The extraction may also include preparing a dried extract by drying, e.g., through nitrogen drying or lyophilization, the obtained extract. The extract may be redissolved in an appropriate solvent after drying, if necessary.

The composition may further include a fraction of the extract. The term "fraction" refers to a substance, or a fractionated material, wherein the components of the *Aucuba japonica* extract are separated by fractionation. The fraction may be obtained by solvent fractionation. The solvent fractionation may refer to mixing the *Aucuba japonica* extract to be fractionated with a solvent and separating the substance present in the solvent. In the present disclosure, the extract is not to be construed as a pure extract that excludes fractions unless expressly stated otherwise.

The composition may contain the *Aucuba japonica* extract in an amount of 0.001-80 wt %, e.g., 0.01-60 wt %, 0.01-40 wt %, 0.01-30 wt %, 0.01-20 wt %, 0.01-10 wt %, 0.01-5 wt %, 0.05-60 wt %, 0.05-40 wt %, 0.05-30 wt %, 0.05-20 wt %, 0.05-10 wt %, 0.05-5 wt %, 0.1-60 wt %, 0.1-40 wt %, 0.1-30 wt %, 0.1-20 wt %, 0.1-10 wt % or 0.1-5 wt %, based on the total weight of the composition.

The composition may contain the extract in an effective amount or as an effective ingredient depending on purposes. The effective amount may be selected appropriately depending on individuals. The effective amount may be determined according to such factors as the severity of a disease or a condition, the age, body weight, health, sex and sensitivity of an individual to the extract, administration time, administration route, rate of excretion, duration of administration, other compositions used in combination with the extract, and other factors well known in the field of physiology or medicine.

When the composition is a composition for a functional health food, it can be formulated into a typical functional health food formulation known in the art. The composition for a functional health food may be prepared as common formulations such as a powder, a granule, a tablet, a pill, a capsule, a suspension, an emulsion, a syrup, an infusion, a liquid, an extract, etc., and may be prepared in the form of any health food such as meat, sausage, bread, chocolate, candy, snack, confectionery, pizza, ramen other noodles, gum, jelly, dairy products including ice cream, various soups, beverages, tea, drinks, alcoholic beverages, vitamin complexes, etc. A sitologically acceptable carrier or additive may be used for the formulation of the health food, and any carrier or additive known to be usable in the art for the preparation of the formulation to be prepared may be used. The additive may include various nutrients, vitamins, electrolytes, flavors, colorants, pectic acid and its salts, alginic acid and its salts, organic acids, protective colloidal thickeners, pH adjusting agents, stabilizers, preservatives, glycerin, carbonating agents used in carbonated drinks, etc. In addition, the composition may contain a pulp for preparing natural fruit juice, fruit juice beverages and vegetable beverages. These additive components may be used independently or in combination, and the proportion of the additive may be 0.001-5 wt %, or 0.01-3 wt %, based on the total weight of the composition.

The content of the extract in the functional health food composition may be determined adequately according to the intended use (prevention or alleviation). Generally, it may contain 0.01-15 wt % of the extract based on the total food weight. When it is prepared as a beverage, it may contain 0.02-10 g, specifically 0.3-1 g, of the extract based on 100 mL of the composition. The beverage may further contain ingredients other than the extract, and may further contain various flavors or natural carbohydrates commonly used in beverages. Examples of the natural carbohydrate include common sugars such as monosaccharides (e.g., glucose, fructose, etc.), disaccharides (e.g., maltose, sucrose, etc.) polysaccharides (e.g., dextrin, cyclodextrin, etc.) and sugar alcohols such as xylitol, sorbitol, erythritol, etc. In addition, as the flavoring, a natural flavor (e.g., thaumatin, stevia extract, etc.) or a synthetic flavor (e.g., saccharin, aspartame, etc.) may be contained. The ratio of the natural carbohydrate may be generally about 1-20 g, specifically about 5-12 g, per 100 mL of beverage.

When the composition is a pharmaceutical composition, it may contain a pharmaceutically acceptable diluent or carrier. The diluent may be lactose, corn starch, soybean oil, microcrystalline cellulose, mannitol, or a lubricant such as magnesium stearate, talc or a combination thereof. The carrier may be an excipient, a disintegrant, a binder, a lubricant or a combination thereof. The excipient may be microcrystalline cellulose, lactose, low-substituted hydroxycellulose or a combination thereof. The disintegrant may be calcium carboxymethyl cellulose, sodium starch glycolate, anhydrous calcium monohydrogen phosphate or a combination thereof. The binder may be polyvinylpyrrolidone, low-substituted hydroxypropyl cellulose, hydroxypropyl cellulose or a combination thereof. The lubricant may be magnesium stearate, silicon dioxide, talc or a combination thereof. The pharmaceutical composition may contain the extract in an effective amount or as an active ingredient. The effective amount may be selected appropriately depending on individuals depending on the severity of a disease, the age, body weight, health, sex and sensitivity to the extract of a patient, administration time, administration route, excretion rate, duration of treatment, drugs used in the combination the composition, and other factors well known in the medical field.

The inventors of the present disclosure have identified through experiments that an extract or a fraction of *Aucuba japonica* significantly prevents decrease of tear secretion amount and corneal morphological change caused by dry eye syndrome and exhibits an effect similar to that of drugs commonly used for the treatment of dry eye syndrome. Accordingly, the *Aucuba japonica* extract can be usefully used to prevent, alleviate or treat dry eye syndrome.

Advantageous Effects

An *Aucuba japonica* extract can be usefully used to prevent, alleviate or treat dry eye syndrome.

BRIEF DESCRIPTION OF DRAWINGS

FIG. 2A shows images showing the state of corneal surface depending on the administration of an *Aucuba japonica* extract.

BEST MODE

Figure 1:
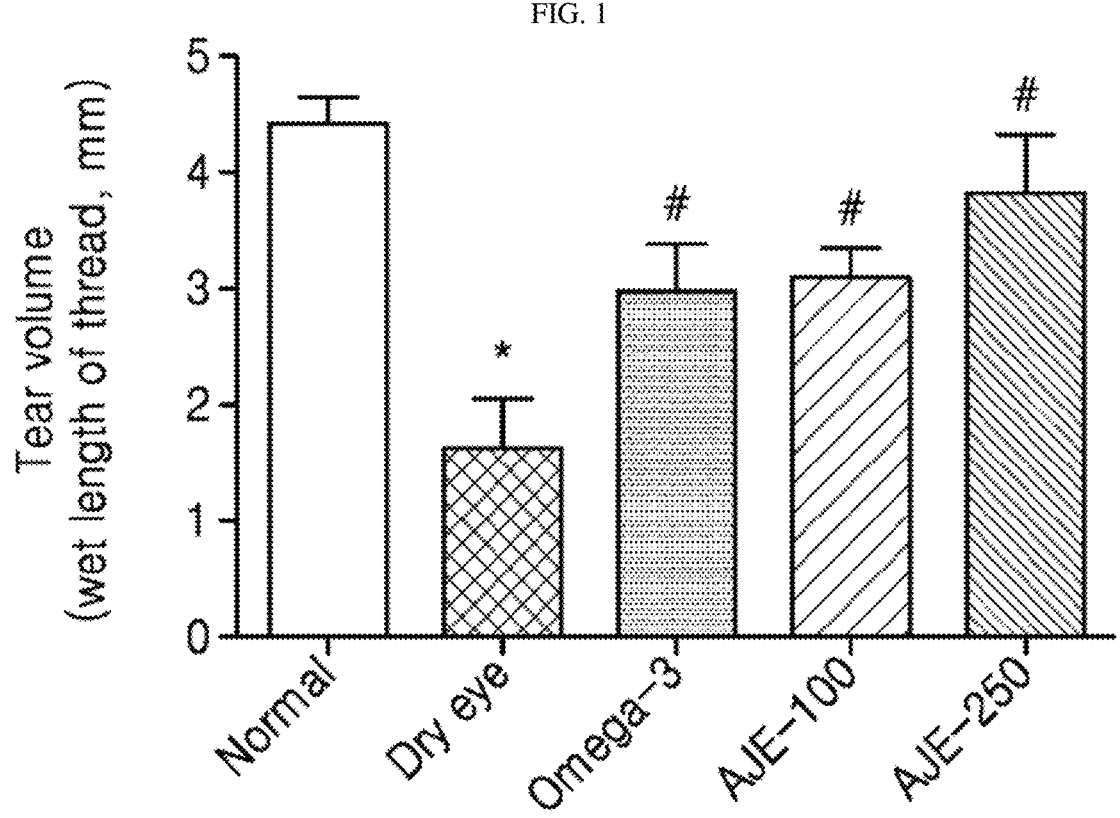
FIG. 1 shows the change in the amount of tear secretion depending on the administration of an *Aucuba japonica* extract.

Hereinafter, the present disclosure is described in more detail through examples. However, these examples are for illustrative purposes only and the scope of the present disclosure is not limited by these examples.

Example 1. Preparation of Reflux Extract of *Aucuba japonica*

The leaf and stem of *Aucuba japonica* were collected two times, in June and September of 2017, at two places around Donnaeko Valley (Sanghyo-dong, Seogwipo-si, Jeju Special Self-Governing Province, Korea) and one place near Songdang-ri Haeoreum (Gujwa-eup, Jeju-si). The samples are kept in a sample storage room of Jeonbuk University.

Then, 50 g of the *Aucuba japonica* (a mixture of leaf and stem) was added to 1500 mL of 30% ethanol (w/w) and a 30% ethanol reflux extract was obtained by conducting reflux extraction once at 100° C. for 3 hours.

Example 2. Preparation of Hot Water Extract of *Aucuba japonica*

The leaf and stem of *Aucuba japonica* were collected two times, in June and September of 2017, at two places around Donnaeko Valley (Sanghyo-dong, Seogwipo-si, Jeju Special Self-Governing Province, Korea) and one place near Songdang-ri Haeoreum (Gujwa-eup, Jeju-si). The samples are kept in a sample storage room of Jeonbuk University.

Then, after adding 900 mL of distilled water to 50 g of the *Aucuba japonica* (a mixture of leaf and stem), an *Aucuba japonica* hot water extract was obtained by conducting extraction at 100° C. for 3 hours, concentration under reduced pressure, and drying.

Example 3. Analysis of Aucubin Content Through HPLC Analysis of *Aucuba japonica* Extract The content of aucubin contained in the *Aucuba japonica* extract was analyzed by high-performance liquid chromatography-diode array detection (HPLC-DAD; Shimadzu HPLC system, Shimadzu, Kyoto, Japan). The result is shown in Table 1.

TABLE 1

| Extract | Aucubin content (mean ± SD, n = 3) | |
|---|---|---|
| | mg/g | % |
| 30% ethanol extract | 305.69 ± 2.68 | 30.57 |
| Hot water extract | 159.82 ± 2.07 | 15.98 |

Example 4. Evaluation of the Function of *Aucuba japonica* Extract In Vivo Using Dry Eye Syndrome Model Animal 4.1 Experimental Animal and Experiment Design Six-week-old SD rats were purchased from Orient and accustomed for one week. One week later, the exorbital lacrimal gland was surgically removed under deep anesthesia to induce dry eye syndrome. After one week, after contacting a phenol red thread for tear volume measurement (FCI Ophthalmic Zone Quick, Japan) to the ocular surface at the outer end of the eyelid, the length of the wetted thread was measured 30 seconds later. Among the rats, only the individuals with significantly decreased tear secretion levels compared to a non-treated group were selected for a drug efficacy test. After groping, drugs prepared for the respective groups were administered once a day for 5 days, and omega-3, a drug used for dry eye syndrome, was used as a control drug. The breeding of the experimental animals and all experimental procedures using the experimental animals were approved by the Institutional Animal Care and Use Committee of the Korea Institute of Oriental Medicine and were carried out according to guidelines.

4.2 Analysis of Tear Volume and Corneal Damage

The amount of tear secretion was measured by contacting a phenol red thread for tear volume measurement (FCI Ophthalmic Zone Quick, Japan) to the ocular surface at the outer end of the eyelid and measuring the length of the wetted thread 30 seconds later. Corneal damage due to dryness was analyzed by photographing the cornea using a ring-type light illuminator and assessing the degree of corneal damage due to dryness.

4.3 Experimental Results 4.3.1 Increased Amount of Tear Secretion

A 30% ethanol extract of *Aucuba japonica* was orally administered to the dry eye syndrome-induced animal model at concentrations of 100 and 250 mg/kg/day, respectively, for 5 days. Then, the amount of tear secretion was measured. As shown in FIG. 1, it was confirmed that the amount of tear secretion was significantly increased by the administration of the *Aucuba japonica* extract. In particular, when compared with omega-3, which is typically used for the treatment of dry eye syndrome, the administration of the *Aucuba japonica* extract showed a better effect than the omega-3.

4.3.2 Alleviated Corneal Damage

In dry eye syndrome, corneal damage is induced due to a lack of tears. Therefore, the effect of the 30% ethanol extract of *Aucuba japonica* on the alleviation of corneal damage was evaluated using the above-described animal model.

Figure 2B:
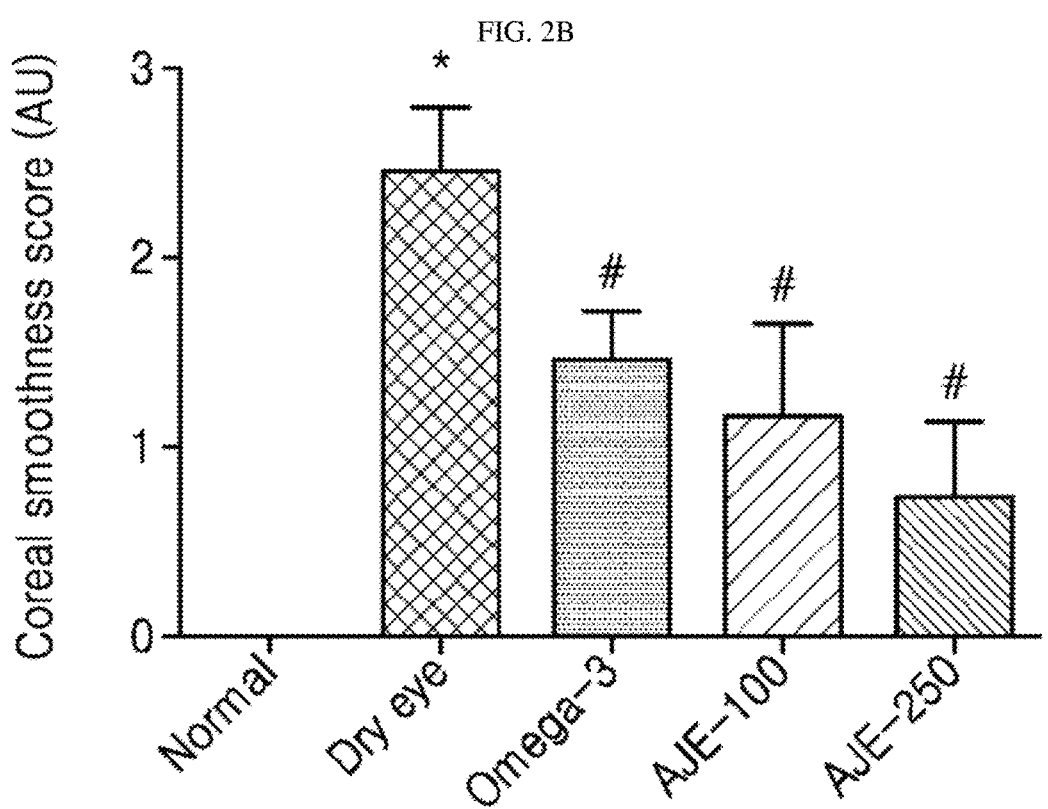
FIG. 2B quantitatively shows the degree of recovery from corneal damage depending on the administration of an *Aucuba japonica* extract as corneal smoothness scores.

As a result, the normal group maintained the smooth and flat surface state of the cornea because the tear film was formed normally as shown in FIG. 2A. Meanwhile, the dry eye syndrome group showed rough corneal surface because the corneal epithelial cells were damaged due to insufficient tear film formation and the rough surface resulted in an irregularly distorted pattern. In contrast, the distortion caused by corneal damage was significantly inhibited in the *Aucuba japonica* extract-administered group, and the efficacy was superior to that of the control drug, omega-3. FIG. 2B quantitatively shows the degree of corneal damage as corneal smoothness scores.

The invention claimed is:

1. A method for treating dry eye syndrome, comprising administering a therapeutically effective amount of an *Aucuba japonica* extract to a subject in need of treating the dry eye syndrome, wherein the *Aucuba japonica* extract comprises aucubin.

2. The method for treating dry eye syndrome according to claim 1, wherein the *Aucuba japonica* extract is an ethanol extract or a hot water extract.

3. The method for treating dry eye syndrome according to claim 2, wherein the ethanol extract is a 20-40% ethanol (w/w) extract.

4. The method for treating dry eye syndrome according to claim 2, wherein the hot water extract is extracted at a temperature of 90-120° C.

5. The method for treating dry eye syndrome according to claim 1, wherein the *Aucuba japonica* extract is administered orally.

6. The method for treating dry eye syndrome according to claim 1, wherein the *Aucuba japonica* extract is an extract of the leaf or stem of *Aucuba japonica*.

7. A method for increasing tear secretion amount, comprising administering a therapeutically effective amount of an *Aucuba japonica* extract to a subject in need of increasing the tear secretion amount, wherein the *Aucuba japonica* extract comprises aucubin.

8. The method for increasing tear secretion amount according to claim 7, wherein the *Aucuba japonica* extract is an ethanol extract or a hot water extract.

9. The method for increasing tear secretion amount according to claim 8, wherein the ethanol extract is a 20-40% ethanol (w/w) extract.

10. The method for increasing tear secretion amount according to claim 8, wherein the hot water extract is extracted at a temperature of 90-120° C.

11. The method for increasing tear secretion amount according to claim 7, wherein the *Aucuba japonica* extract is administered orally.

12. The method for increasing tear secretion amount according to claim 7, wherein the *Aucuba japonica* extract is an extract of the leaf or stem of *Aucuba japonica*.

13. A method for treating corneal morphological change, comprising administering a therapeutically effective amount of an *Aucuba japonica* extract to a subject in need of treating the corneal morphological change, wherein the *Aucuba japonica* extract comprises aucubin.

14. The method for treating corneal morphological change according to claim 13, wherein the *Aucuba japonica* extract is an ethanol extract or a hot water extract.

15. The method for treating corneal morphological change according to claim 14, wherein the ethanol extract is a 20-40% ethanol (w/w) extract.

16. The method for treating corneal morphological change according to claim 14, wherein the hot water extract is extracted at a temperature of 90-120° C.

17. The method for treating corneal morphological change according to claim 13, wherein the *Aucuba japonica* extract is administered orally.

18. The method for treating corneal morphological change according to claim 13, wherein the *Aucuba japonica* extract is an extract of the leaf or stem of *Aucuba japonica*.

* * * * *